United States Patent
Kurosaki et al.

(10) Patent No.: US 11,690,983 B2
(45) Date of Patent: Jul. 4, 2023

(54) DRUG LAYER APPLYING DEVICE AND METHOD FOR FORMING DRUG LAYER

(71) Applicant: TERUMO KABUSHIKI KAISHA, Tokyo (JP)

(72) Inventors: Yasuo Kurosaki, Kanagawa (JP); Hiroshi Goto, Kanagawa (JP); Yuno Kitagawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 375 days.

(21) Appl. No.: 16/879,169

(22) Filed: May 20, 2020

(65) Prior Publication Data
US 2020/0276421 A1 Sep. 3, 2020

Related U.S. Application Data (63) Continuation of application No. PCT/JP2018/043181, filed on Nov. 22, 2018.

(30) Foreign Application Priority Data

Nov. 22, 2017 (JP) ................ 2017-224340

(51) Int. Cl.
*A61M 25/10* (2013.01)
*A61M 25/00* (2006.01)

(52) U.S. Cl.
CPC ...... *A61M 25/1029* (2013.01); *A61M 25/104* (2013.01); *A61L 2420/02* (2013.01);
(Continued)

(58) Field of Classification Search
CPC .... A61M 2025/105; A61M 2025/1031; A61M 2025/0019; A61M 2025/0056;
(Continued)

(56) References Cited

U.S. PATENT DOCUMENTS 3,690,294 A * 9/1972 Harper .................. D04H 3/12
118/325
5,531,828 A * 7/1996 Whang ................. B43M 11/04
156/441.5
(Continued)

FOREIGN PATENT DOCUMENTS

CN 101941287 A 1/2011
CN 202290443 U 7/2012
(Continued)

OTHER PUBLICATIONS

Office Action (Notice of Reasons for Refusal) dated May 10, 2022, by the Japanese Patent Office in corresponding Japanese Patent Application No. 2019-555365 and an English Translation of the Office Action. (6 pages).
(Continued)

*Primary Examiner* — Nathan J Jenness
*Assistant Examiner* — Thomas Chiang
(74) *Attorney, Agent, or Firm* — Buchanan Ingersoll & Rooney PC (57) ABSTRACT

Provided are a drug layer applying device and a method for forming a drug layer which can quickly and easily apply or provide an appropriate amount of a drug on a surface of a medical instrument such as a balloon. A drug layer applying device that applies a drug layer on a surface of a balloon to be inserted into a living body, includes: a deformable porous body capable of holding a coating solution containing a drug and a solvent; a removal unit that is flexibly deformable and arranged alongside the porous body; and a holding base that holds the porous body and the removal unit.

16 Claims, 6 Drawing Sheets

(52) U.S. Cl.
CPC .............. *A61M 2025/0019* (2013.01); *A61M 2025/105* (2013.01); *A61M 2025/1031* (2013.01)

(58) Field of Classification Search
CPC .. A61M 2025/1075; A61M 2025/1086; A61M 25/1038; A61M 25/1029; A61M 25/0045; A61M 25/104; A61L 2400/00; A61L 2400/02; B05C 3/09; B05C 5/0241; B05C 7/00; B05C 7/20; B05C 1/02; B05C 13/02
See application file for complete search history.

(56) References Cited

U.S. PATENT DOCUMENTS

| | | | |
|---|---|---|---|
| 2012/0100279 A1* | 4/2012 | Neumann | B05C 3/09 118/58 |
| 2014/0004253 A1 | 1/2014 | Ruane | |
| 2014/0272164 A1* | 9/2014 | Mcevoy | B05C 1/06 118/264 |
| 2014/0370067 A1 | 12/2014 | Margraf et al. | |
| 2014/0371837 A1 | 12/2014 | Huang et al. | |
| 2018/0221631 A1 | 8/2018 | Ruane | |
| 2020/0164185 A1* | 5/2020 | Walsh | A61M 25/1038 |
| 2020/0282188 A1 | 9/2020 | Kitagawa et al. | |
| 2020/0282190 A1 | 9/2020 | Kurosaki et al. | |

FOREIGN PATENT DOCUMENTS

| | | |
|---|---|---|
| CN | 102802816 A | 11/2012 |
| CN | 105413951 A | 3/2016 |
| CN | 106064127 A | 11/2016 |
| DE | 10 2012 001 216 A1 | 7/2013 |
| JP | H0382480 A | 4/1991 |
| JP | H04200479 A | 7/1992 |
| JP | 3168406 U | 6/2011 |
| JP | 2012100762 A | 5/2012 |
| JP | 2015119804 A | 7/2015 |
| JP | 2016182183 A | 10/2016 |
| JP | 2016187628 A | 11/2016 |

OTHER PUBLICATIONS

Office Action (The Second Office Action) dated May 7, 2022, by the State Intellectual Property Office of People's Republic of China in corresponding Chinese Patent Application No. 201880075563.3 and an English Translation of the Office Action. (12 pages).
U.S. Appl. No. 16/879,002, filed May 20, 2020, Yasuo Kurosaki et al.
U.S. Appl. No. 16/879,277, filed May 20, 2020, Yuno Kitagawa et al.
International Search Report (PCT/ISA/210) dated Feb. 5, 2019, by the Japanese Patent Office as the International Searching Authority for International Application No. PCT/JP2018/043181.
Written Opinion (PCT/ISA/237) dated Feb. 5, 2019, by the Japanese Patent Office as the International Searching Authority for International Application No. PCT/JP2018/043181.
Office Action (The First Office Action) dated Aug. 18, 2021, by the State Intellectual Property Office of People's Republic of China in corresponding Chinese Patent Application No. 201880075563.3 and an English Translation of the Office Action. (12 pages).
An English Translation of the International Search Report (Form PCT/ISA/210) and the Written Opinion of the International Searching Authority (Form PCT/ISA/237) dated Feb. 5, 2019, by the Japanese Patent Office in corresponding International Application No. PCT/JP2018/043181. (13 pages).

* cited by examiner

DRUG LAYER APPLYING DEVICE AND METHOD FOR FORMING DRUG LAYER

CROSS-REFERENCES TO RELATED APPLICATIONS

This application is a continuation of International Patent Application No. PCT/JP2018/043181 filed on Nov. 22, 2018, which claims priority to Japanese patent Application No. 2017-224340 filed on Nov. 22, 2017, the entire content of both of which is incorporated herein by reference.

FIELD OF THE INVENTION

The present invention generally relates to a drug layer applying device that applies or provides a drug layer on a surface of a medical instrument such as a balloon, and a method for forming a drug layer.

BACKGROUND DISCUSSION

In recent years, a balloon catheter has been used to improve a lesion (stenotic part) present in a body lumen. The balloon catheter typically includes an elongated shaft portion and a radially inflatable balloon provided on a distal side or distal portion of the shaft portion. When the deflated balloon is inflated after reaching a target location in a body via a living body lumen, a lesion can be pushed to be widened.

However, when the lesion is forcibly pushed to be widened, smooth muscle cells may excessively proliferate to cause new stenosis (restenosis) at the lesion in some cases. Therefore, recently, a drug eluting balloon (DEB) in which a surface of a balloon is coated with a drug for suppressing stenosis has been used. The drug eluting balloon inflates to instantaneously release, to the lesion, the drug which has been applied to the surface of the balloon, thereby suppressing restenosis.

Japanese Patent Application Publication No. 2015-119804 discloses an example of a method for forming a drug layer on a surface of the balloon that involves applying a coating liquid containing a drug to a rotating balloon using a porous body such as a sponge and performing drying to form a drug layer.

SUMMARY

In the method described in Japanese Patent Application Publication No. 2015-119804, the coating liquid is applied to the balloon by bringing the porous body such as the sponge containing the coating liquid into contact with the balloon that rotates about an axis. Therefore, a device for rotating the balloon is required, and it is difficult to easily apply the drug on the balloon.

Disclosed here is a drug layer applying device and a method for forming a drug layer which can quickly and easily provide or apply an appropriate amount of a drug on a surface of a medical instrument.

A drug layer applying device to apply a drug layer on a surface of a medical instrument to be inserted into a living body includes: a deformable porous body configured to hold a coating solution containing a drug and a solvent; a removal unit that is flexibly deformable and arranged alongside the porous body; and a holding base that holds the porous body and the removal unit.

A method for forming a drug layer on a surface of a medical instrument to be inserted into a living body so that a drug exists on the surface of the medical instrument includes: bringing the medical instrument, after having been removed from the living body after use in the living body, into contact with a deformable porous body that holds a coating solution containing a drug and a solvent, and applying the coating solution to the surface of the medical instrument; and drying the solvent in the coating solution applied to the surface of the medical instrument.

The drug layer applying device configured as described above can remove blood or the like from the used medical instrument using the removal unit, and can apply the coating solution to the medical instrument using the porous body. Therefore, an appropriate amount of the drug layer can be quickly and easily formed on the surface of the medical instrument.

The drug layer applying device may further include a powdered drug held by the porous body. As a result, the powdered drug can be dissolved in the solvent by supplying the solvent to the porous body, so that the coating solution held by the porous body can be obtained.

The porous body may have a concave portion configured to receive the medical instrument. As a result, the medical instrument hardly deviates from the concave portion by arranging the medical instrument in the concave portion, and a contact area between the porous body and the medical instrument increases. Therefore, the coating solution can be effectively applied to the surface of the medical instrument.

The drug layer applying device may include a heating unit that heats the porous body, and a pressurizing unit that pressurizes the porous body. As a result, an adhesive force between the medical instrument and the drug can be enhanced, and the drop of the drug from the medical instrument can be suppressed.

The removal unit may have a removal concave portion configured to receive the medical instrument to be arranged. As a result, blood or the like on the surface of the medical instrument can be effectively removed by arranging the medical instrument in the removal concave portion.

The holding base may have a recessed portion, and the porous body may be positioned in the recessed portion. As a result, it is difficult for the coating solution to leak out of the porous body, and the porous body is easily brought into contact with the medical instrument. Therefore, the coating solution can be effectively applied to the surface of the medical instrument.

The holding base may be deformable so as to close an entrance of the recessed portion. As a result, the porous body can be pressed against the surface of the medical instrument by deforming the holding base, and the coating solution can be effectively applied.

The medical instrument may be a balloon configured to inflate and deflate. As a result, the appropriate amount of the drug layer can be quickly and easily applied on the surface of the balloon.

The drug in the drug layer may contain at least one selected from the group including rapamycin, paclitaxel, docetaxel, and everolimus. As a result, restenosis of a stenotic part in a blood vessel can be favorably suppressed by the drug layer.

The drug in the drug layer may contain at least one selected from the group including a water-insoluble drug, a water-soluble drug, and a hydrophilic polymer. As a result, it is possible to apply, to the drug layer, a drug that is appropriate for conditions and the like, alone or in combination, from various drugs.

In the method for forming a drug layer as described above, the coating solution can be applied to the used medical instrument using the porous body. Therefore, the appropriate amount of the drug layer can be quickly and easily applied on the surface of the medical instrument.

The method for forming a drug layer may involve removing blood from the surface of the medical instrument using a flexibly deformable removal unit, provided alongside the porous body, prior to the applying of the coating solution to the surface of the medical instrument. As a result, the removal unit can remove blood or the like from the used medical instrument, and the coating solution can be favorably applied to the used medical instrument to form the drug layer.

The medical instrument may be a balloon capable of inflating and deflating, guidewire, guiding sheath, guiding catheter, or stent. As a result, it is possible to quickly and easily apply or provide an appropriate amount of the drug layer on a surface of the balloon, the guidewire, the guiding sheath, the guiding catheter, or the stent. If the medical instrument is the balloon, the appropriate amount of the drug layer can be quickly and easily apply on the surface of the balloon. In addition, the balloon used for pre-dilation of a target site in the living body can be removed, and then, the drug layer can be apply on the same balloon to reuse the balloon for post-dilation of the target site.

BRIEF DESCRIPTION OF THE DRAWINGS

FIGS. 2A and 2B are front views illustrating the drug layer applying device, in which FIG. 2A illustrates a state before a holding base is closed, and FIG. 2B illustrates a state where the holding base is closed.

FIGS. 5A and 5B are front views illustrating a distal portion of the balloon catheter, in which FIG. 5A illustrates a state where the balloon is deflated, and FIG. 5B illustrates a state where the balloon is inflated.

FIGS. 7A and 7B are cross-sectional views illustrating a state at the time of applying a coating solution to the balloon by the drug layer applying device, in which FIG. 7A is a state before the coating solution is applied to the balloon, and FIG. 7B is a state where the coating solution is applied to the balloon.

FIGS. 9A and 9B are perspective views illustrating a first modification of the drug layer applying device, in which FIG. 9A illustrates a state where an entrance of the holding base is open, and FIG. 9B illustrates a state where the entrance of the holding base is narrowed.

DETAILED DESCRIPTION

Set forth below with reference to the accompanying drawings is a detailed description of embodiments of a drug layer applying device and method of forming or applying a drug layer on a surface of a medical instrument to be inserted into a living body, representing examples of the inventive drug layer applying device and method disclosed here. Dimensional ratios of the drawings are exaggerated for the convenience of description and may differ from actual ratios in some cases.

A drug layer applying device 10 according to the embodiment is a device configured to apply a drug layer on a surface of a balloon 70 (see FIG. 3), which is inserted into a stenotic part of a living body lumen, such as a blood vessel, to push and widen the stenotic part, thereby forming a drug-eluting balloon as illustrated in FIGS. 1 to 4. A medical instrument on which the drug layer applying device 10 applies the drug layer is not limited to the balloon 70, and may be, for example, a guide wire, a guiding sheath, a guiding catheter, a stent, or the like. The description below will describe an example in which the drug layer is applied on the balloon 70 by the drug layer applying device 10.

Figure 1:
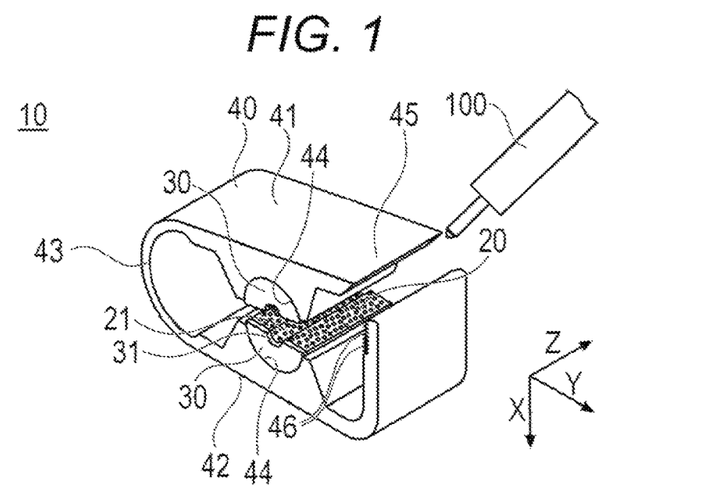
FIG. 1 is a perspective view illustrating a drug layer applying device according to an embodiment.

The drug layer applying device 10 includes a porous body 20, a removal unit 30, and a holding base 40.

The holding base 40 holds the porous body 20 and the removal unit 30. The holding base 40 is a substantially C-shaped member that is deformable. The holding base 40 includes a first holding portion 41 and a second holding portion 42 that can approach and separate from each other (are movable toward and away from one another), and a connecting portion 43 that connects the first holding portion 41 and the second holding portion 42 to each other.

Figure 2A:
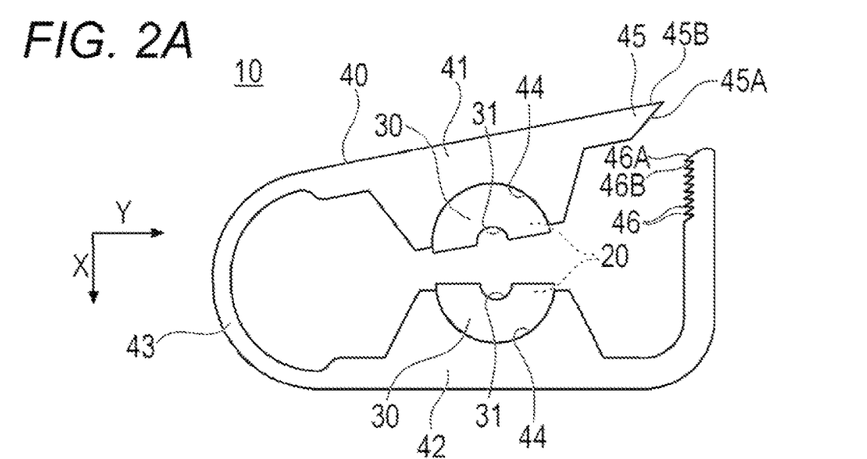
Figure 2B:
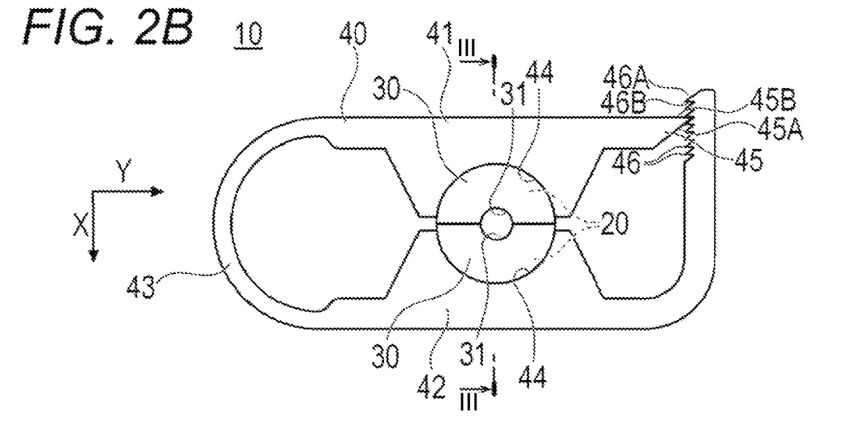
Figure 3:
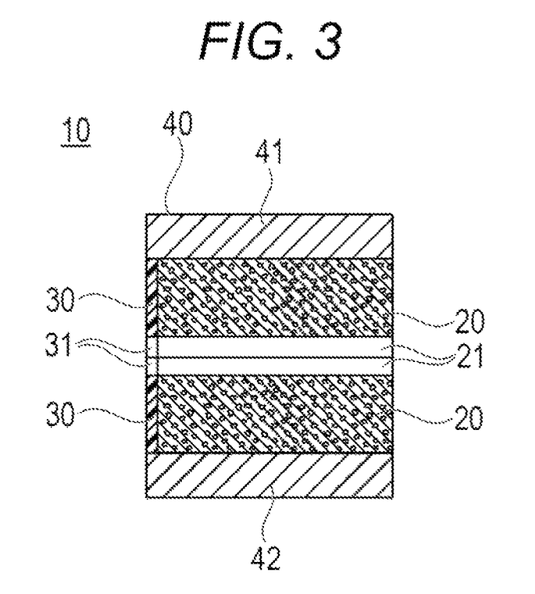
FIG. 3 is a cross-sectional view taken along the section line III-III of FIG. 2B.

Opposing surfaces of the first holding portion 41 and the second holding portion 42 have recessed portions 44 that house or hold the porous body 20 and the removal unit 30, respectively. The recessed portions 44 may be concave-shaped as illustrated in FIGS. 1, 2A and 2B.

A claw portion 45, which protrudes in a direction Y orthogonal to a direction X in which the first holding portion 41 is movable with respect to the second holding portion 42, is formed at an end of the first holding portion 41. The claw portion 45 has a first inclined surface 45A that is inclined with respect to the moving direction X of the first holding portion 41 on the side of the claw portion closer to the second holding portion 42. The claw portion 45 has a first orthogonal surface 45B, substantially orthogonal to the moving direction X of the first holding portion 41, on the side of the claw portion facing away from the second holding portion 42.

A plurality of spaced-apart locking portions 46 that can be brought into contact with the claw portion 45 and protrude to the opposite side of the protruding direction Y of the claw portion 45 (i.e., the locking portions 46 protrude in a direction opposite the direction of protrusion of the claw portion 45) are formed at an end of the second holding portion 42. The plurality of locking portions 46 each have a second inclined surface 46A that is inclined with respect to the moving direction X of the first holding portion 41 on the side of the locking portion 46 closer to the first holding portion 41. The locking portion 46 has a second orthogonal surface 46B, substantially orthogonal to the moving direction X of the first holding portion 41, on the side of the locking portion 46 facing away from the first holding portion 41. The plurality of locking portions 46 are arranged side by side in the moving direction X of the first holding portion 41.

The connecting portion 43 is located between the first holding portion 41 and the second holding portion 42, and is thinner than the first holding portion 41 and the second holding portion 42. Therefore, the connecting portion 43 can be deformed and bent such that the first holding portion 41 and the second holding portion 42 approach and move away from each other. In a state where the connecting portion 43 is not deformed, that is, in a natural state where no external force acts on the connecting portion 43, the first holding portion 41 is separated from the second holding portion 42, and the claw portion 45 is not in contact with the locking portion 46 (see FIGS. 1 and 2A).

The recessed portion 44 is formed in a groove shape in the direction Z through which an internal space of the holding base 40 penetrates. The direction Z is substantially orthogonal to both the moving direction X of the first holding portion 41 and the protruding direction Y of the claw portion 45.

A constituent material from which the holding base 40 may be fabricated preferably has flexibility. Examples of such materials from which the holding base 40 may be fabricated include polyurethane, ABS, polypropylene, polycarbonate, nylon, polyethylene, polyacetal, stainless steel, polyethylene terephthalate (PET), silicon, Teflon, and the like.

The porous body 20 is a sponge-like member that can be flexibly deformed and can hold a liquid containing a drug. The porous body 20 is arranged in the recessed portion 44 of the first holding portion 41 and the recessed portion 44 of the second holding portion 42. In the illustrated embodiment, the porous body is comprised of two porous bodies 20. Each of the porous bodies 20 has a groove-shaped concave portion 21 extending in the direction Z. The concave portions 21 of the respective porous bodies 20 can overlap each other (e.g., may be aligned with one another) when the first holding portion 41 and the second holding portion 42 approach each other.

Examples of a constituent material from which the porous body 20 may be fabricated include foamed polyurethane, polyethylene foam, polyurethane foam, polypropylene foam, EVA cross-linked foam, PET resin foam, phenol foam, silicone foam, cellulose, chloroprene rubber, fluorine rubber, nitrile rubber, and the like.

The removal unit 30 functions as a wiper to wipe-off or remove a liquid such as blood. The removal unit 30 is a plate-shaped member that is flexibly deformable. The removal unit 30 is arranged in the recessed portion 44 of the first holding portion 41 and the recessed portion 44 of the second holding portion 42. It is preferable that the removal unit 30 not be porous. In the illustrated embodiment, the removal unit is comprised of two removal units 30. Each of the removal units 30 is arranged on one end surface side (i.e., at one axial end) of one of the porous bodies 20 alongside the porous body 20. Each of the removal units 30 includes a surface to be contacted by a groove-like removal concave portion 31 extending in the direction Z. The removal concave portions 31 of the respective removal units 30 are arranged side by side so as to communicate with the concave portions 21 of the adjacent porous bodies 20. The removal concave portions 31 of the respective removal units 30 can overlap each other (e.g., may be aligned with one another) when the first holding portion 41 and the second holding portion 42 approach each other.

Examples of a constituent material from which the removal unit 30 may be fabricated include various rubber materials such as natural rubber, silicone rubber, butyl rubber, isoprene rubber, butadiene rubber, and styrene-butadiene rubber, various thermoplastic elastomers such as polyurethanes, polyesters, polyamides, olefins, and styrenes or a mixture thereof, nonwoven fabric, nylon, and the like.

A coating solution containing a drug and a solvent is supplied to the porous body 20 from a solution supply unit 100 such as a syringe (see FIG. 1) and is held in the porous body 20. The drug contained in the coating solution may be a water-soluble drug or a water-insoluble drug. A water-insoluble drug means a drug that is insoluble or poorly soluble in water, and specifically solubility in water may be less than 1 mg/mL, and further, may be less than 0.1 mg/mL. Water-insoluble drugs include fat-soluble drugs. A form of the water-insoluble or water-soluble drug is not particularly limited, and may be, for example, a crystal or not.

Some preferred examples of the water-insoluble drug include immunosuppressants, for example, cyclosporines containing cyclosporine, immunoadjuvants such as rapamycin, carcinostatics such as paclitaxel, antiviral agents or antibacterial agents, antineoplastic agents, analgesic agents and anti-inflammatory agents, antibiotics, antiepileptics, anxiolytic agents, antiparalytic agents, antagonists, neuron blocking agents, anticholinergic agents and cholinergic agents, muscarine antagonists agents and muscarine agents, antiadrenergic agents, antiarrhythmic agents, antihypertensive agents, hormone preparations, and nutritional supplements.

The water-insoluble drug is preferably at least one selected from the group including rapamycin, paclitaxel, docetaxel, and everolimus. The rapamycin, paclitaxel, docetaxel, and everolimus in the present specification include their analogs and/or derivatives as long as the analogs and/or derivatives have equivalent drug effect. For example, paclitaxel and docetaxel are in an analog relation. Rapamycin and everolimus are in a derivative relation among these, paclitaxel is more preferable.

The water-soluble drug may be a drug having solubility in water of 1 mg/mL or more, preferably 5 mg/mL or more, more preferably 10 mg/mL or more, and still more preferably 33 mg/mL or more. Water-soluble antiplatelet drugs include clopidogrel sulfate, ticlopidine hydrochloride, prasugrel hydrochloride, sarpogrelate hydrochloride, and the like (incidentally, water-insoluble antiplatelet drugs include aspirin, cilostazol, ticagrelor, and the like). Examples of the water-soluble anticoagulant include warfarin, edoxaban tosilate hydrate, heparin, dabigatran etexilate methanesulfonate, and the like. The drug may also be a hydrophilic polymer, and a wet coating using the hydrophilic polymer (the coating that exhibits lubricity when wetted with water) is possible. The drug may be applied as the hydrophilic polymer. on a surface (inner and outer surfaces) of a medical instrument to be inserted into a blood vessel (for example, a guidewire, a guiding sheath, a guiding catheter, or the like) without being limited to the surface (inner and outer surfaces) of the balloon catheter.

Preferably, the solvent is an organic solvent. The organic solvent preferably has a quick-drying property, and examples thereof include tetrahydrofuran, acetone, glycerin, ethanol, methanol, dichloromethane, hexane, ethyl acetate, and the like. The solvent may include water.

The coating solution may contain an additive (excipient). When the coating solution contains the additive, examples of the additive include a water-soluble low molecular weight compound and the like. A molecular weight of the water-soluble low molecular weight compound is 50 to 2,000, preferably 50 to 1,000, more preferably 50 to 500, and still more preferably 50 to 200. An amount of the water-soluble low molecular weight compound is preferably 10 to 5,000 parts by weight, more preferably 50 to 3000 parts by weight, and still more preferably 100 to 1000 parts by weight, per 100 parts by weight of the water-insoluble drug. The constituent material of the water-soluble low molecular weight compound is serine ethyl ester, sugars such as glucose, sugar alcohols such as sorbitol, citrate, polysorbate, polyethylene glycol, urea, Water-soluble polymers, a contrast agent, an amino acid ester, a glycerol ester of a short-chain monocarboxylic acid, a pharmaceutically acceptable salt, and a surfactant, or a mixture of two or more of these can be used. The water-soluble low molecular weight compound has a hydrophilic group and a hydrophobic group, and is characterized by being soluble in water. The water-soluble low molecular weight compound is preferably non-swellable or hardly swellable. The additive containing the water-soluble low molecular weight compound has an effect of uniformly dispersing the water-insoluble drug on the surface of the balloon 70. It is preferable that the additive be not a hydrogel. The additive contains the low molecular weight compound, and thus, dissolves quickly without swelling when coming into contact with an aqueous solution. Further, the additive easily dissolves when the balloon 70 is inflated in the blood vessel so that crystal particles of the water-insoluble drug on the surface of the balloon 70 are easily released, and thus, there is an effect of increasing the number of the crystal particles of the drug adhering to the blood vessel.

The water-soluble low molecular weight compound has a molecular weight of 50 to 2,000, and is dissolved at an amount of 1 mg/mL or more in water, preferably dissolved at an amount of 5 mg/mL or more in water, more preferably dissolved at an amount of 10 mg/mL or more in water, still more preferably dissolved at an amount of 33 mg/mL or more in water, and preferably dissolved in water without inflating. It is preferable that the water-soluble low molecular weight compound be not a hydrogel. The water-soluble low molecular weight compound is preferably not a polymer, and more preferably not a water-insoluble polymer. It is preferable that the water-soluble low molecular weight compound be not polyethylene glycol (PEG) and a water-soluble PEG (for example, polyethylene glycol 200-600).

The solubility of a substance can be defined as a degree of dissolution within 30 minutes at 20° C. For example, the solubility of a substance can be defined by an amount of solvent (for example, an amount of water) required to dissolve 1 g (or 1 mL) of solute. When the amount of solvent required to dissolve 1 g of solute is less than 1 mL, the solute is extremely soluble in the solvent. In this case, the dissolved amount is more than 1000 mg/mL. Examples of such a substance include sorbitol, urea, and glycerol. When the amount of solvent required to dissolve 1 g of solute is 1 mL or more and less than 10 mL, the solute is freely soluble in the solvent. In this case, the dissolved amount is more than 100 mg/mL and 1000 mg/mL or less. Examples of such a substance include polysorbate, an amino acid ester, polyethylene glycol 200-600, a serine ethyl ester, a contrast agent (iopromide), and a water-soluble polymer. When the amount of solvent required to dissolve 1 g of solute is 10 mL or more and less than 30 mL, the solute is soluble in the solvent. In this case, the dissolved amount is more than 33 mg/mL and 100 mg/mL or less. Examples of such a substance include polyethylene glycol. When the amount of solvent required to dissolve 1 g of solute is 30 mL or more and less than 100 mL, the solute is slightly soluble in the solvent. In this case, the dissolved amount is more than 10 mg/mL and 33 mg/mL or less. When the amount of solvent required to dissolve 1 g of solute is 100 mL or more and less than 1000 mL, the solute is sparingly soluble in the solvent. In this case, the dissolved amount is more than 1 mg/mL and 10 mg/mL or less. When the amount of solvent required to dissolve 1 g of solute is 1000 mL or more and less than 10,000 mL, the solute is extremely insoluble in the solvent. In this case, the dissolved amount is more than 0.1 mg/mL and 1 mg/mL or less. When the amount of solvent required to dissolve 1 g of solute is 10,000 mL or more, the solute is hardly soluble in the solvent. In this case, the dissolved amount is 0.1 mg/mL or less. Examples of such a substance include a fatty acid ester of glycerin. The water-soluble substance refers to a substance other than a substance that is "extremely insoluble" and a substance that is "hardly soluble". Specifically, the water-soluble substance indicates a substance that is "extremely soluble", a substance that is "freely soluble", a substance that is "slightly soluble", and a substance that is "sparingly soluble". The water-soluble substance preferably indicates a substance that is "extremely soluble", a substance that is "freely soluble" and a substance that is "slightly soluble".

Figure 4:
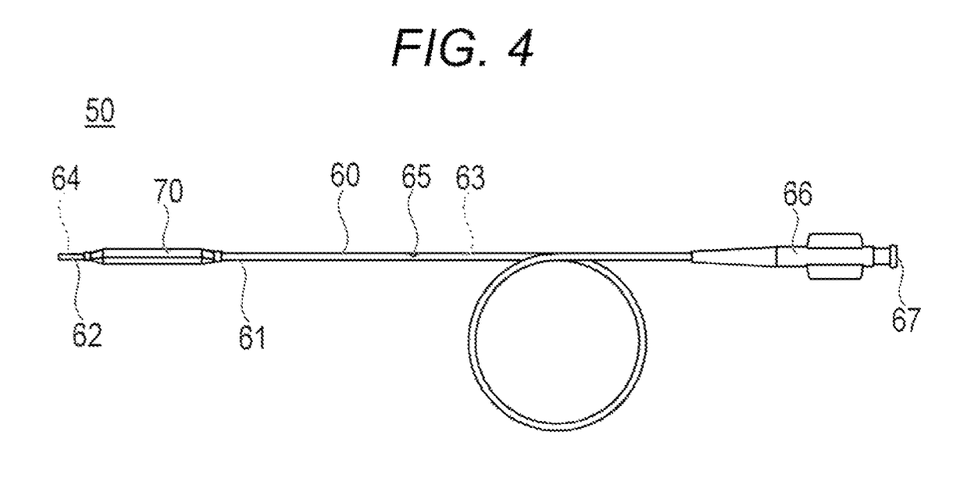
FIG. 4 is a front view illustrating a balloon catheter.
Figure 5A:
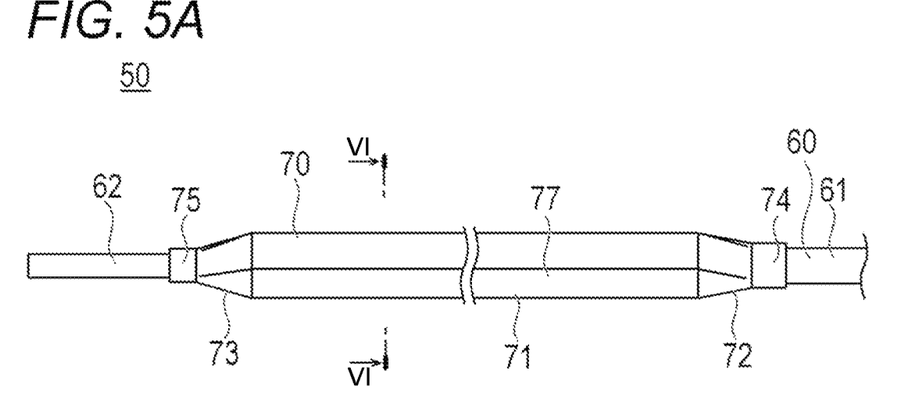
Figure 5B:
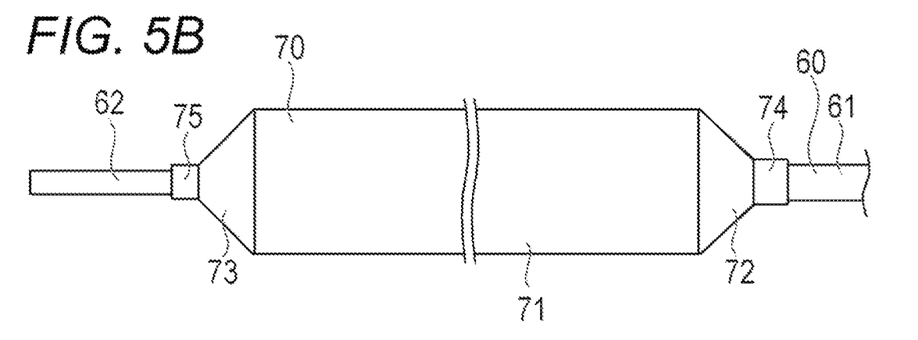
Figure 6:
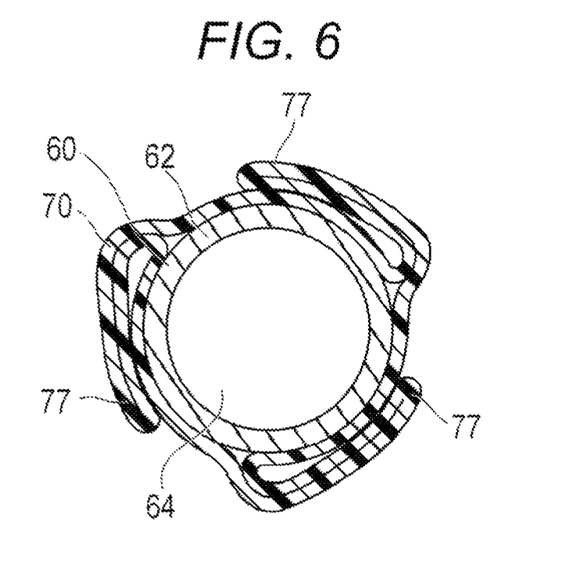
FIG. 6 is a cross-sectional view taken along line VI-VI of FIG. 5A.

Next, a balloon catheter 50 on which a drug is applied using the drug layer applying device 10 will be described with reference to FIGS. 4 to 6. In the present specification, a side of the balloon catheter 50 to be inserted into a living body lumen is referred to as a "distal side" or "distal end" and an operating hand side of the balloon catheter 50 is referred to as a "proximal side" or "proximal end".

The balloon catheter 50 includes an elongated shaft portion 60, the balloon 70 provided at a distal portion of the shaft portion 60, and a hub 66 fixed to a proximal end of the shaft portion 60.

The shaft portion 60 includes an outer tube 61 that is a tubular body of which distal end and proximal end are open, and an inner tube 62 that is a tubular body arranged inside the outer tube 61. The inner tube 62 is housed in a hollow interior of the outer tube 61, and the shaft portion 60 has a double-tube structure at the distal portion. The hollow interior of the inner tube 62 is a guide wire lumen 64 through which a guide wire is inserted. An inflation lumen 63 for circulating inflation fluid of the balloon 70 is formed in the hollow interior of the outer tube 61 outside the inner tube 62. The inner tube 62 is open to the outside at a side opening 65. The inner tube 62 protrudes further to the distal side from the distal end of the outer tube 61. That is, the inner tube 62 protrudes distally beyond the distal-most end of outer tube 61. A distal tip, which is a separate member, may be provided at a distal portion of the inner tube 62.

The balloon 70 includes: a straight portion or intermediate portion 71 formed in a main body in the axial direction; a proximal tapered portion 72 located on the proximal side of the straight portion 71; and a distal tapered portion 73 located on the distal side of the straight portion 71. The straight portion 71 has a cylindrical shape that has substantially the same outer diameter along its entire length when inflated. An outer diameter of the proximal tapered portion 72 gradually decreases from the straight portion 71 toward the proximal side. An outer diameter of the distal tapered portion 73 gradually decreases from the straight portion 71 toward the distal side.

The straight portion 71 is a portion of the balloon 70 where the drug is applied by the drug layer applying device 10. The range in which the drug is applied by the drug layer applying device 10 is not limited only to the straight portion 71, but may include at least a part of the proximal tapered portion 72 and the distal tapered portion 73 in addition to the straight portion 71. Alternatively, the range in which the drug is applied by the drug layer applying device 10 may be only a part of the straight portion 71.

In the balloon 70, a balloon fusing portion 74 located at the proximal end of the proximal tapered portion 72 is fused to the distal portion of the outer tube 61. In addition, a balloon fusing portion 75 located at the distal end of the distal tapered portion 73 is fused to the distal portion of the inner tube 62 in the balloon 70. A method for fixing the balloon 70 to the outer tube 61 and the inner tube 62 is not limited to fusion, but may be, for example, adhesion. As a result, the inside of the balloon 70 communicates with the inflation lumen 63. The balloon 70 can be inflated by injecting the inflation fluid into the balloon 70 via the inflation lumen 63. The inflation fluid may be a gas or a liquid, and, for example, a gas such as a helium gas, a $CO_2$ gas, an $O_2$ gas, an $N_2$ gas, an Ar gas, air, and a mixed gas, or a liquid such as physiological saline and a contrast agent can be used.

The balloon 70 has a plurality of pleats 77 shaped to protrude in the radial direction. The pleats 77 can be folded in the circumferential direction. The pleats 77 are each formed by a fold extending substantially in the axial direction of the balloon 70. The length of each pleat 77 in the long-axis direction does not exceed the length of the balloon 70. The number of the pleats 77 is not particularly limited, and is one to seven, for example, but is three in the present embodiment. The plurality of pleats 77 are preferably arranged to be uniform in the circumferential direction of the balloon 70, but are not limited thereto.

The length of the balloon 70 in the axial direction is not particularly limited, but is preferably 5 to 500 mm, more preferably 10 to 300 mm, and still more preferably 20 to 200 mm. The outer diameter of the balloon 70 when inflated is not particularly limited, but is preferably 1 to 10 mm, and more preferably 2 to 8 mm.

It is preferable that the balloon 70 have a certain degree of flexibility and a certain degree of hardness such that the balloon 70 can be inflated when reaching a blood vessel, a tissue, or the like, and release the drug on the outer surface of the balloon 70. Specifically, the balloon 70 is made of metal or resin, but it is preferable that at least the surface of the balloon 70 be made of resin. As a constituent material of at least the surface of the balloon 70, for example, polyolefins such as polyethylene, polypropylene, polybutene, an ethylene-propylene copolymer, an ethylene-vinyl acetate copolymer, and an ionomer, or a mixture of two or more kinds thereof, thermoplastic resins such as soft polyvinyl chloride resin, polyamide, a polyamide elastomer, a nylon elastomer, polyester, a polyester elastomer, polyurethane, and a fluororesin, a silicone rubber, a latex rubber, and the like can be used. Among them, polyamides are preferably used.

In the hub 66, a proximal opening 67, which communicates with the inflation lumen 63 of the outer tube 61 and functions as a port for inflow and outflow of the inflation fluid, is formed.

Next, an operation of the drug layer applying device 10 according to the present embodiment will be described.

First, the balloon 70 that has been used for pre-dilation of a stenotic part such as a blood vessel is deflated and removed from the blood vessel. As a result, blood or the like adheres to the surface of the balloon 70.

Next, the coating solution containing the drug and the solvent is supplied to the porous body 20 from the solution supply unit 100, such as a syringe, as illustrated in FIG. 1. As a result, the porous body 20 is in the state of holding the coating solution.

Figure 7A:
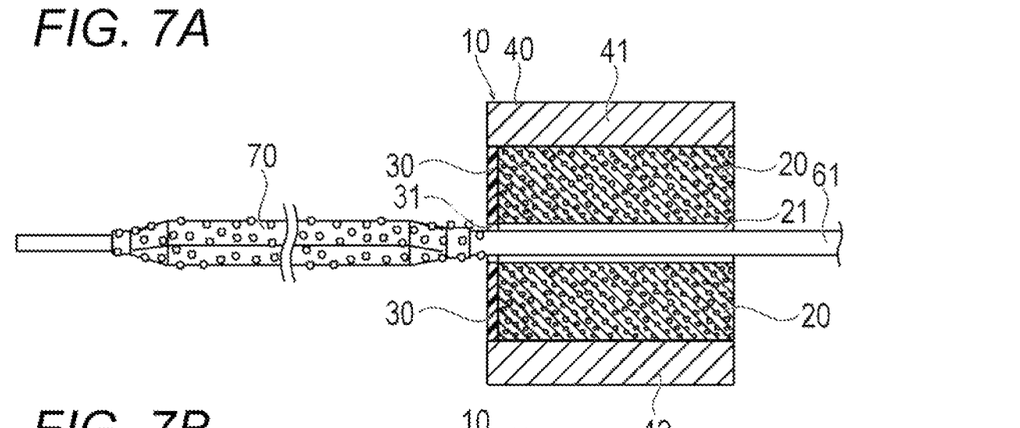

Next, the outer tube 61 of the balloon catheter 50 is housed inside the holding base 40 from a gap between the claw portion 45 and the locking portion 46 in the separated state. At this time, the removal unit 30 is located on the side close to the balloon 70, and the porous body 20 is located on the side close to the hub 66. Then, the outer tube 61 is housed in the removal concave portion 31 and the concave portion 21, and outer surfaces of the first holding portion 41 and the second holding portion 42 are gripped and pressed, as illustrated in FIG. 7A. As a result, the connecting portion 43 deflects, the first holding portion 41 and the second holding portion 42 approach each other, and the first inclined surface 45A of the claw portion 45 is brought into contact with the second inclined surface 46A of the locking portion 46, as illustrated in FIG. 2B. When the outer surfaces of the first holding portion 41 and the second holding portion 42 are further pressed, the first inclined surface 45A advances over the second inclined surface 46A. As a result, the first orthogonal surface 45B of the claw portion 45 can come into contact with the second orthogonal surface 46B. Since the first orthogonal surface 45B and the second orthogonal surface 46B are substantially orthogonal to the moving direction X of the first holding portion 41, the claw portion 45 that has advanced over the locking portion 46 in the moving direction X is suppressed or prevented from returning to the opposite side in the moving direction X. Therefore, the claw portion 45 is locked by the locking portion 46, and a distance between the first holding portion 41 and the second holding portion 42 is fixed. The claw portion 45 can be locked to or engaged with any of the locking portions 46. Therefore, the claw portion 45 can be locked to or engaged with the desired locking portion 46 by moving the claw portion 45 in the moving direction X to the desired locking portion 46. As a result, the distance between the first holding portion 41 and the second holding portion 42 can be appropriately adjusted in accordance with a size of the balloon 70 (and a size of the outer tube 61). The porous body 20 and the removal unit 30 can be appropriately deformed depending on positions of the first holding portion 41 and the second holding portion 42. After the claw portion 45 is locked by the locking portion 46, the claw portion 45 can be separated from the locking portion 46 by deforming the second holding portion 42 in the protruding direction Y of the claw portion 45 such that the locking portion 46 is separated from the claw portion 45.

Figure 7B:
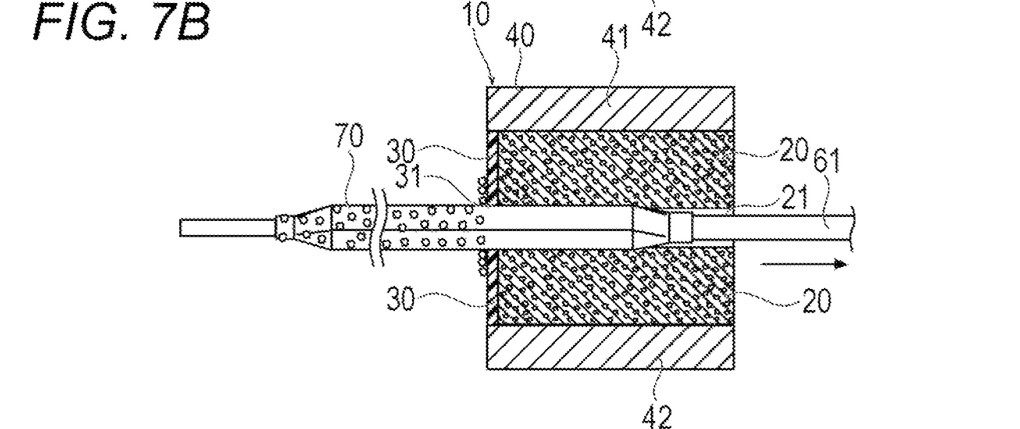
Figure 8:
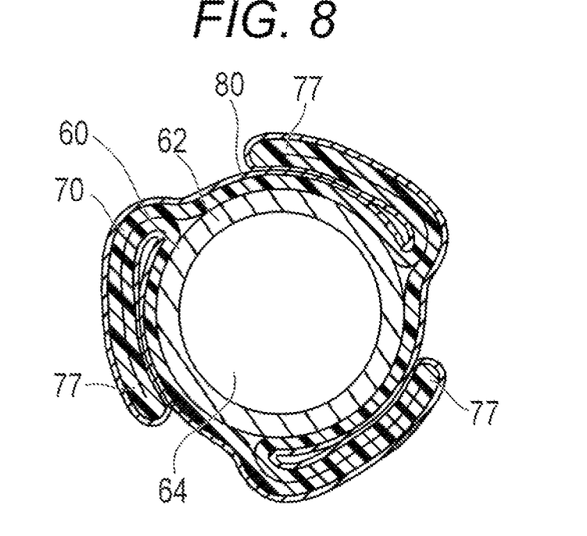
FIG. 8 is a cross-sectional view illustrating the balloon on which a drug layer is formed.

Next, the balloon 70 is moved to the relatively proximal side with respect to the drug layer applying device 10 as illustrated in FIG. 7B. That is, the balloon 70 and the drug layer applying device 10 are relatively moved so that the balloon 70 moves in the proximal direction and enters the drug layer applying device 10. As a result, the removal unit 30 (surface of the wiper) comes into contact with the surface of the balloon 70. Therefore, the blood or the like adhering to the outer surface of the balloon 70 is removed by the removal unit 30. The balloon 70 from which the blood or the like has been removed then comes into contact with the exposed surface of the porous body 20 that is arranged alongside the removal unit 30. As a result, the coating solution containing the drug is applied to the surface of the balloon 70. The coating solution is a liquid, and thus, can also enter a gap between the folded pleats 77 of the balloon 70. The solvent of the coating solution is evaporated after completely withdrawing the balloon 70 from the drug layer applying device 10. As a result, a drug layer 80 containing a drug is formed or exists on the surface of the balloon 70 as illustrated in FIG. 8. If the coating solution includes an additive, the drug layer 80 includes the additive. Thereafter, the balloon 70 having the drug layer 80 is inserted again into a blood vessel and is inflated, whereby a stenotic part can be expanded while causing the drug to act on a living tissue.

As described above, the drug layer applying device 10 according to the present embodiment is the drug layer applying device 10 configured to form or apply the drug layer 80 on the surface of the balloon 70 (medical instrument) to be inserted into the living body, and includes: the deformable porous body 20 capable of holding the coating solution containing the drug and the solvent; the removal unit 30 that is flexibly deformable and is arranged alongside the porous body 20; and the holding base 40 that holds the porous body 20 and the removal unit 30.

The drug layer applying device 10 configured as described above can remove the blood or the like from the used balloon 70 using the removal unit 30 and can apply the coating solution to the balloon 70 using the porous body 20. Therefore, the appropriate amount of the drug layer 80 can be quickly and easily formed on the surface of the balloon 70.

The porous body 20 has the concave portion 21 which allows the balloon 70 to be arranged or properly positioned relative to the porous body. As a result, the balloon 70 hardly deviates from the concave portion 21 by arranging the balloon 70 in the concave portion 21, and the contact area between the porous body 20 and the balloon 70 increases. Therefore, the coating solution can be effectively applied to the surface of the balloon 70.

The removal unit 30 has the removal concave portion 31 which allows the balloon 70 to be arranged or properly positioned relative to the removal unit. As a result, the balloon 70 is arranged in the removal concave portion 31, and the blood or the like on the surface of the balloon 70 can be effectively removed.

The holding base 40 has the recessed portion 44, and the porous body 20 is arranged inside the recessed portion 44. As a result, it is difficult for the coating solution to leak out of the porous body 20, and the porous body 20 is easily brought into contact with the balloon 70. Therefore, the coating solution can be effectively applied to the surface of the balloon 70.

The medical instrument to which the coating solution is applied is the balloon 70 that is capable of inflating and deflating. As a result, the appropriate amount of the drug layer 80 can be quickly and easily applied on the surface of the balloon 70.

The drug in the drug layer 80 may contain at least one selected from the group including rapamycin, paclitaxel, docetaxel, and everolimus. As a result, restenosis of a stenotic part in a blood vessel can be favorably suppressed by the drug layer 80.

The drug in the drug layer 80 may contain at least one selected from the group including a water-insoluble drug, a water-soluble drug, and a hydrophilic polymer. As a result, it is possible to apply, to the drug layer 80, a drug that is appropriate for conditions and the like, alone or in combination, from various drugs.

The present invention also includes a method for forming a drug layer to apply a drug on a surface of the balloon 70 (medical instrument) to be inserted into a living body. The method for forming a drug layer includes: applying a coating solution to the surface of the balloon 70 by bringing the balloon 70 having been removed out of the living body after use in the living body into contact with the deformable porous body 20 that holds the coating solution containing the drug and a solvent; and a step of drying the solvent.

In the method for forming a drug layer configured as described above, the coating solution can be applied to the used balloon 70 using the porous body 20. Therefore, the appropriate amount of the drug layer 80 can be quickly and easily formed on the surface of the balloon 70.

The method for forming a drug layer may include removing blood from the surface of the balloon 70 using the flexibly deformable removal unit 30, provided alongside the porous body 20, prior to applying the coating solution to the surface of the balloon 70. As a result, the removal unit 30 can remove the blood or the like from the used balloon 70, and the coating solution can be favorably applied to the used balloon 70 to form the drug layer 80.

The medical instrument is the balloon 70 that is capable of inflating and deflating. As a result, the appropriate amount of the drug layer 80 can be quickly and easily applied on the surface of the balloon 70. In addition, the balloon 70 used for pre-dilation of a target site in the living body can be removed, and then, the drug layer 80 can be applied on the same balloon 70 to reuse the balloon 70 for post-dilation of the target site. The drug layer applying device 10 may be used to form the drug layer 80 on the balloon 70 before being inserted into the living body.

The present invention is not limited to only the above-described embodiment, and various modifications can be made by those skilled in the art within a technical idea of the present invention. For example, the balloon catheter 50 is a rapid exchange type, but may be an over-the-wire type.

Figure 9A:
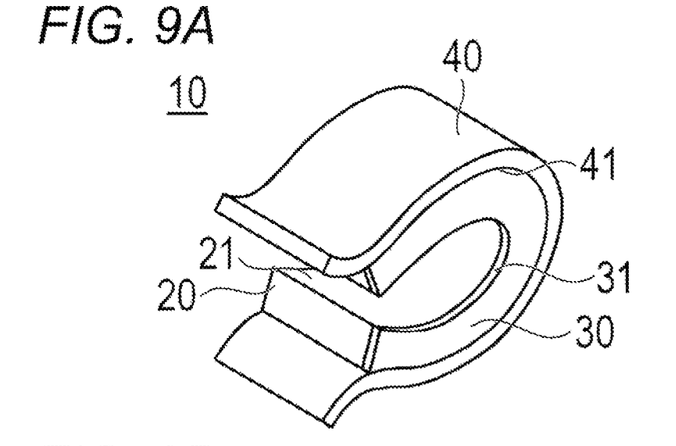
Figure 9B:
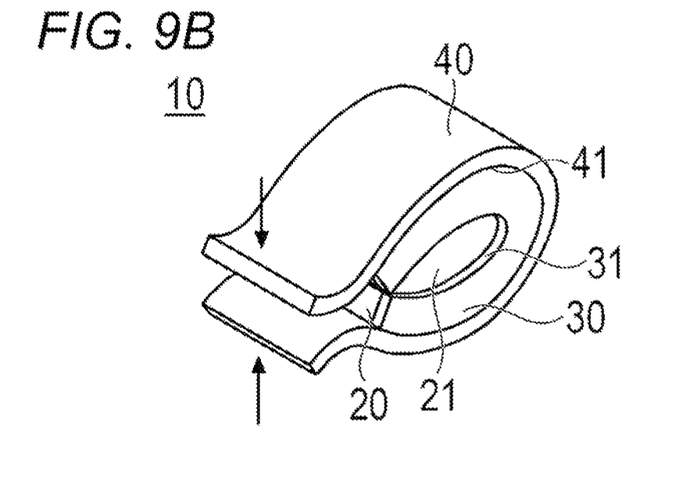

In addition, the drug layer applying device 10 may be configured such that the recessed portion 44 is formed inside the substantially C-shaped holding base 40, and the substantially C-shaped porous body 20 and removal unit 30 are arranged in the recessed portion 44 as in a first modification illustrated in FIG. 9A. When an outer surface of the substantially C-shaped holding base 40 is pressed to reduce the internal space, the concave portion 21 of the porous body 20 and the removal concave portion 31 of the removal unit 30 can be narrowed as illustrated in FIG. 9B. As a result, the shapes of the porous body 20 and the removal unit 30 can be appropriately adjusted in accordance with a size of the balloon 70.

Figure 10:
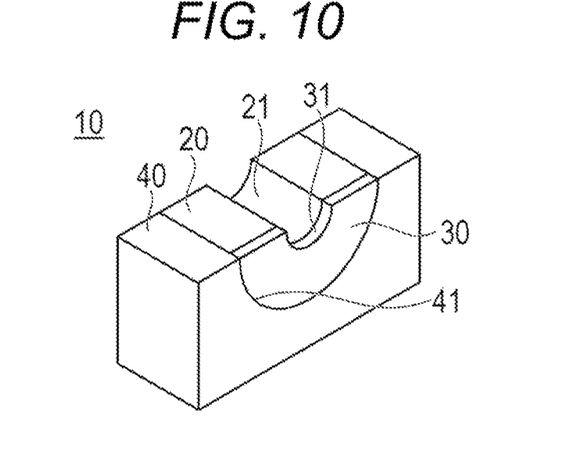
FIG. 10 is a perspective view illustrating a second modification of the drug layer applying device.

In addition, the drug layer applying device 10 may be configured such that the concave portion 21 of the porous body 20 and the removal concave portion 31 of the removal unit 30 arranged in the recessed portion 44 of the holding base 40 have shapes that surround only a range of about 180 degrees of the balloon 70 as in a second modification illustrated in FIG. 10. The holding base 40 is not deformed. Even with such a configuration, when the balloon 70 is moved to the proximal side or in the proximal direction with respect to the drug layer applying device 10 while rotating the balloon 70, blood or the like can be removed from the surface of the balloon 70 using the removal unit 30, and the coating solution can be applied to the balloon 70 using the porous body 20.

Figure 11:
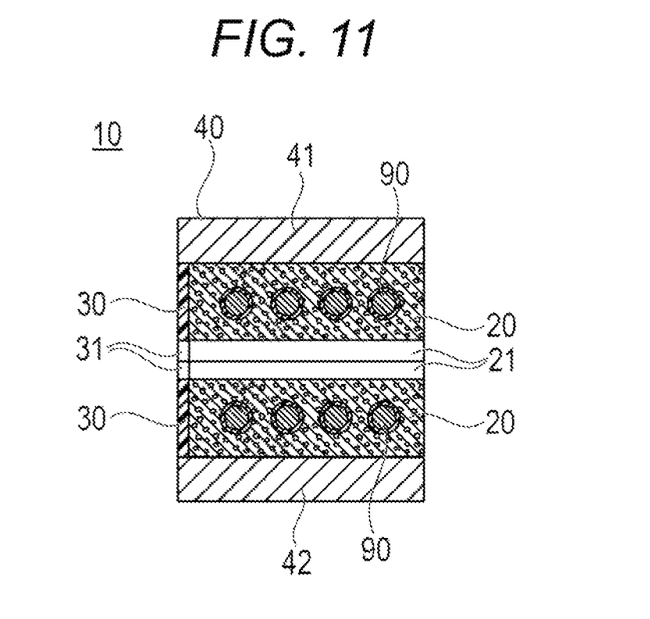
FIG. 11 is a cross-sectional view illustrating a third modification of the drug layer applying device.

The drug layer applying device 10 may include a heating unit 90 that can heat the porous body 20 as in a third modification illustrated in FIG. 11. The heating unit 90 is a heating wire embedded in the porous body 20 and has an outer surface covered so as not to come into direct contact with the porous body 20. The heating unit 90 as the heating wire is supplied with a current from the outside. Alternatively, the heating unit 90 as the heating wire is supplied with a current from a battery (not illustrated) provided in the drug layer applying device 10. The heating unit 90 can increase a bonding force between the balloon 70 and the drug by heating. A heating temperature using the heating unit 90 can be, for example, 30 to 80° C., but is preferably 30 to 60° C. A hydrophilic polymer (wet coating) applied to the surface of the medical instrument such as the balloon 70 can be fixed to the surface of the medical instrument by heating.

The configuration of the heating unit is not particularly limited. For example, the heating unit may be a pipe that circulates a heated fluid in the porous body 20 or to a side opposite to a side on which the drug is applied (for example, a position away from the porous body 20 and opposing the porous body 20 in FIG. 10), or a heating plate which is arranged by being heated by a heating wire or a heated fluid. The drug layer applying device 10 can heat the porous body 20 to strengthen the bonding force between the drug and the balloon 70, and can further cover and tighten the balloon 70 with the heated porous body 20. That is, the porous body 20 can also function as a pressurizing unit that can tighten the balloon 70.

Figure 12:
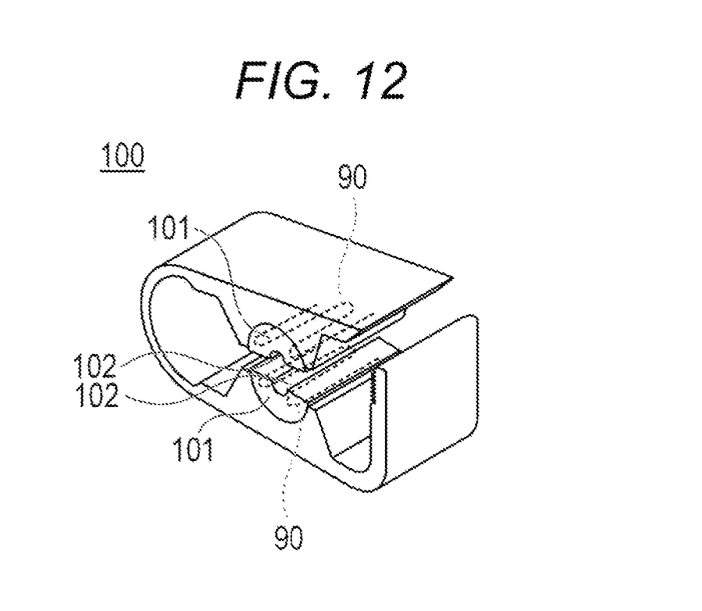
FIG. 12 is a perspective view illustrating a fourth modification of the drug layer applying device.

In addition, the drug layer applying device may further include another device 100 including the heating unit 90 and pressurizing units 101 in addition to the above-described device including the porous body 20 (see FIG. 1) as in a fourth modification illustrated in FIG. 12. This device 100 includes the pair of pressurizing units 101 in which concave portions 102 sandwiching the balloon 70, coated with a drug by the porous body 20, are formed. The pressurizing unit 101 can approach and separate (move towards and away) from each other. Although a structure of the device 100 other than the pressurizing unit 101 is substantially the same as the device illustrated in FIG. 1, the structure of the device 100 is not particularly limited. A constituent material for fabricating the pressurizing unit 101 is preferably a material such as Teflon that prevents peeling of the drug applied to the balloon 70. Alternatively, a Teflon film may be arranged at a portion of the pressurizing unit 101 that is in contact with the balloon 70. The heating unit 90 is embedded in the pressurizing unit 101.

The device 100 heats and pressurizes the balloon 70, coated with the drug through the porous body 20 of the device illustrated in FIG. 1, using the heated pressurizing unit 101. As a result, an adhesive force between the balloon 70 and the drug can be strengthened, and the adhesive force between the balloon 70 and the drug can be further enhanced to reduce the crossing profile (outer diameter) of the balloon 70. As a result, the detachment of the drug from the balloon 70 can be prevented. In addition, when the balloon catheter 50 is reused, it is possible to easily apply the drug to the balloon 70 and fold the balloon 70 by combining a part to be heated and a part to be pressurized. In addition, since the balloon 70 can be shaped by folding with the heating and pressurization, it is also possible to mitigate an insertion resistance to the blood vessel.

Although no gap is formed between the removal unit 30 and the porous body 20 in each of the above-described embodiments, such a gap may be provided. In addition, the removal unit 30 need not necessarily be arranged in the recessed portion 44 of the holding base 40. In addition, the porous body 20 need not necessarily have the concave portion 21, and the removal unit 30 need not necessarily have the removal concave portion 31.

In addition, a powdered drug may be held in the porous body 20 before the coating solution is supplied. The powdered drug is crystalline or amorphous (non-crystalline). As a result, the powdered drug can be dissolved in the solvent by supplying the solvent containing no drug to the porous body 20, so that the coating solution held by the porous body 20 can be obtained.

In addition, the balloon 70 is folded in the deflated state in the balloon catheter 50, but the balloon 70 need not necessarily be folded. That is, the balloon 70 may be formed of a material having elasticity to be inflated while the thickness of the balloon 70 is reduced.

The detailed description above describes embodiments of a drug layer applying device and method of applying a drug layer on a surface of a medical instrument to be inserted into a living body, representing examples of the inventive a drug layer applying device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A combination of a medical instrument, a coating solution and a drug layer applying device,
    the coating solution comprising a drug and a solvent;
    the medical instrument comprising an elongated shaft that is configured to be positioned in a living body to deliver the drug to a part of the living body, the medical instrument possessing an outer surface; and
    the drug layer applying device comprising:
        a base comprised of a first portion and a second portion, the first portion and the second portion each including an axially extending recess;
        a first plate-shaped wiper positioned in the recess in the first portion of the base and a second plate-shaped wiper positioned in the recess in the second portion of the base, the first and second plate-shaped wipers each possessing a surface to be contacted by the outer surface of the medical instrument to remove liquid on the outer surface of the medical instrument;
        a first deformable porous body positioned in the recess in the first portion of the base and a second deformable porous body positioned in the recess in the second portion of the base, the first and second porous bodies each possessing first and second opposite axial ends and being configured to receive the coating solution so that the first porous body and the second porous body each contain the coating solution, the first wiper being positioned adjacent the first axial end of the first porous body and the second wiper being positioned adjacent the first axial end of the second porous body, the first and second porous bodies each possessing an exposed surface to be contacted by the outer surface of the medical instrument after the outer surface of the medical instrument has contacted the wiper to apply the drug to the outer surface of the medical instrument; and
        the base also including a connecting portion that connects the first portion and the second portion to one another and that is configured to: i) allow the first and second portions to move away from one another so that the first and second porous bodies and the first and second wipers also move away from one another to a position in which the first and second porous bodies are completely spaced from one another and the first and second wipers are completely spaced from one another; and ii) to allow the first and second portion that are in the position to move toward one another so the first and second porous bodies move towards one another while the first and second wipers also move towards one another.

2. The combination according to claim 1, wherein the first portion of the base includes a claw and the second portion of the base includes a locking portion, the locking portion and the claw being configured to engage one another and to disengage from one another, the locking portion and the claw being disengaged from one another as the first and second portions of the base move away from one another, the locking portion and the claw engaging one another as the first and second portions of the base move towards one another.

3. The combination according to claim 1, wherein the medical instrument includes an expandable balloon fixed to the elongated shaft, the first and second porous bodies being configured to apply the drug to the outer surface of the balloon.

4. The combination according to claim 1, wherein the exposed surface of the first porous body and the exposed surface of the second porous body each include a concave-shaped recess for receiving the medical instrument.

5. The combination according to claim 4, wherein the surface of the first wiper that is contacted by the outer surface of the medical instrument and the surface of the second wiper that is contacted by the outer surface of the medical instrument each include a concave-shaped recess that is contacted by the outer surface of the medical instrument to remove the liquid on the outer surface of the medical instrument.

6. The combination according to claim 1, wherein the recess in the first portion of the base is a concave-shaped recess and the recess in the second portion of the base is a concave-shaped recess.

7. The combination according to claim 1, wherein the drug contains at least one selected from a group consisting of a water-insoluble drug, a water-soluble drug, and a hydrophilic polymer.

8. The combination according to claim 1, further comprising a heating unit embedded in the first porous body and a heating unit embedded in the second porous body.

9. A drug layer applying device to apply a drug layer on a surface of a medical instrument to be inserted into a living body, the drug layer applying device comprising:
 a first deformable porous body and a second deformable porous body each configured to hold a coating solution containing a drug and a solvent, the first deformable porous body and the second deformable porous body being separate from one another, the first and second porous bodies each possessing first and second opposite axial ends and being configured to receive the coating solution so that the first porous body and the second porous body each contain the coating solution;
 a first plate-shaped wiper and a second plate-shaped wiper that are separate from one another, the first and second plate-shaped wipers each possessing a surface to be contacted by the surface of the medical instrument to remove liquid on the surface of the medical instrument; and
 a holding base comprised of a first portion, a second portion and a connecting portion, the first portion and the second portion of the holding base each including an axially extending recess, the first porous body and the first wiper being positioned in the recess of the first portion of the holding base such that the first wiper is positioned at the first axial end of the first porous body, the second porous body and the second wiper being positioned in the recess of the second portion of the holding base such that the second wiper is positioned at the first axial end of the second porous body, the connecting portion being configured to: i) allow the first and second portions of the holding base to move away from one another so that the first and second porous bodies and the first and second wipers also move away from one another to a position in which the first and second porous bodies are completely spaced from one another and the first and second wipers are completely spaced from one another; and ii) to allow the first and second portion that are in the position to move toward one another so the first and second porous bodies move towards one another while the first and second wipers also move towards one another.

10. The drug layer applying device according to claim 9, further comprising a powdered drug held by the first and second deformable porous bodies.

11. The drug layer applying device according to claim 9, wherein the first porous body and the second porous body each include a concave recess configured to receive the medical instrument.

12. The drug layer applying device according to claim 9, wherein the first wiper and the second wiper each include a concave recess configured to receive the medical instrument.

13. The drug layer applying device according to claim 9, wherein the recess in the first portion of the holding base is concave-shaped recess and the recess in the second portion of the holding base is a concave-shaped recess.

14. The drug layer applying device according to claim 13, wherein the holding base includes an entrance to a location between the first and second porous bodies and between the first and second wipers.

15. The drug layer applying device according to claim 9, further comprising a heating unit embedded in the first porous body and a heating unit embedded in the second porous body.

16. The drug layer applying device according to claim 15, wherein the heating unit embedded in the first porous body is a heating wire and the heating unit embedded in the second porous body is a heating wire.

* * * * *